United States Patent [19]

Gutierrez et al.

[11] 4,324,906

[45] Apr. 13, 1982

[54] CITRIC ACID ESTERS AND PROCESS FOR PRODUCING CITRIC ACID

[75] Inventors: Eddie N. Gutierrez, Fort Lee; Vincent Lamberti, Upper Saddle River, both of N.J.

[73] Assignee: Lever Brothers Company, New York, N.Y.

[21] Appl. No.: 68,043

[22] Filed: Aug. 20, 1979

[51] Int. Cl.³ .................. C07C 69/716; C07C 59/265
[52] U.S. Cl. ..................................... 560/176; 562/584
[58] Field of Search ......................... 560/176; 562/584

[56] References Cited

U.S. PATENT DOCUMENTS

| | | | |
|---|---|---|---|
| 2,017,882 | 10/1935 | Zwilgmeyer et al. | 560/176 |
| 2,594,488 | 4/1952 | Patrick | 560/176 |
| 4,022,803 | 5/1977 | Gutierrez et al. | 260/343.6 |
| 4,056,567 | 11/1977 | Lamberti et al. | 562/584 |
| 4,123,458 | 10/1978 | Gutierrez et al. | 562/595 |
| 4,123,459 | 10/1978 | Gutierrez et al. | 562/595 |
| 4,146,543 | 3/1979 | Gutierrez | 560/176 |
| 4,159,388 | 6/1979 | Gutierrez et al. | 560/192 |

*Primary Examiner*—Natalie Trousof
*Assistant Examiner*—Vera C. Clarke
*Attorney, Agent, or Firm*—Mishrilal L. Jain; James J. Farrell; Melvin H. Kurtz

[57] ABSTRACT

A process is disclosed for converting a compound of the formula

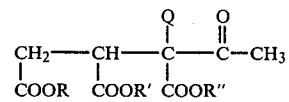

wherein
R and R" are independently methyl, ethyl or propyl;
R' is H, Na, Li, K, Mg$_{\frac{1}{2}}$, Ca$_{\frac{1}{2}}$, Sr$_{\frac{1}{2}}$, Ba$_{\frac{1}{2}}$, methyl, ethyl or propyl; and
Q is chlorine or bromide;

directly to a citrate salt by heating in an aqueous medium, with an alkaline earth metal hydroxide, at a temperature greater than 160° C.

18 Claims, No Drawings

CITRIC ACID ESTERS AND PROCESS FOR PRODUCING CITRIC ACID

This application relates to an improved process for the production of citric acid.

The prior art processes for the production of cirtric acid having generally involved natural fermentation. Some synthetic methods were proposed in the literature, such as: Michael, J., J. Pr. Chem. 49(ii):21 (1894), Pucher and Vickery, J. Biol. Chem. 163:169–184 (1946), and Gawron et al. JACS 80:5856–5860 (1958) but none of these methods appears to have been commercialized.

U.S. Pat. No. 4,056,567, Nov. 1, 1977, discloses a method for the production of citric acid involving heating a specified tricarboxylic acid with an alkaline earth metal hydroxide. This method requires a satisfactory source of cis-aconitic acid, trans-aconitic acid, isocitric acid or alloisocitric acid or mixtures of these.

U.S. Pat. Nos. 4,022,803, May 10, 1977, 4,123,458, Oct. 31, 1978 and application Ser. No. 848,549, filed Nov. 4, 1977 disclose methods for the production of the tricarboxylic acids which can be converted into citric acid by the aforementioned process. U.S. Pat. No. 4,022,803 discloses halogenation of a propane 1,1,2,3-tetracarboxylic compound and conversion of these halogenated compounds to the appropriate tricarboxylates. U.S. Pat. Nos. 4,123,458, 4,159,388 and application Ser. Nos. 905,720, 905,621, 905,676 and 848,549 also disclose novel polyfunctional compounds which may be converted to the tricarboxylic acids through a halogenation step.

It is an object of this invention to eliminate the step of isolation of cis-aconitic acid, trans-aconitic acid, isocitric acid or alloisocitric acid in the production of citric acid.

It is also an object of this invention to provide novel polyfunctional compounds which may be converted to citric acid in a single step.

Other objects and advantages will appear as the description proceeds.

The attainment of the above objects is made possible by a process which involves conversion of compounds of the formula

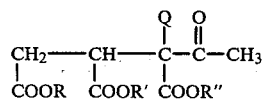

in which
R and R" are independently methyl, ethyl or propyl;
R' is H, Na, Li, K, Mg$\frac{1}{2}$, Ca$\frac{1}{2}$, Sr$\frac{1}{2}$, Ba$\frac{1}{2}$, methyl, ethyl or propyl; and
Q is chlorine or bromine
directly to a citrate by heating in aqueous medium with an excess of alkaline earth metal hydroxide at a temperature of at least 160° C., preferably 160°–300° C., and most preferably 175°–250° C. Thus, there must be more than about 2.5 moles of alkaline earth metal hydroxide per mole of starting material when R' is H, methyl, ethyl or propyl and more than about 2 moles of alkaline earth metal hydroxide per mole of starting material when R' is Na, Li, K, Mg$\frac{1}{2}$, Ca$\frac{1}{2}$, Ba$\frac{1}{2}$ or Sr$\frac{1}{2}$. These conditions correspond to a pH range (measured at 25° C.) of about 11.3 to about 12.5 when Ca(OH)$_2$, Sr(OH)$_2$ or Ba(OH)$_2$ is used and to a pH range of about 9 to about 10 when Mg(OH)$_2$ is used.

The amount of water used should be an excess, but is not critical. The pressure at which the reaction takes place will correspond to the vapor pressure of the aqueous medium which may also contain inert organic liquids which are preferably soluble in the medium and are stable to the alkali conditions of the reaction, for example the lower alkanols, methanol, ethanol, etc. and dioxane.

PREPARATION OF THE STARTING MATERIALS

The starting materials of the present invention (formula I) may be prepared from the di- and tri-esters of acetotricarballylic acid (II):

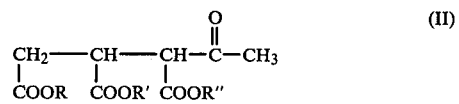

wherein R, R' and R" are as previously defined.

The triethyl ester is known and can be prepared by a conventional Michael reaction set forth in "Maleic Anhydride Derivatives" by Lawrence Flett and William Gardner (John Wiley and Sons, 1952), pp. 68–69. The diester is prepared similarly using a half-salt of maleic acid, but avoiding the highly basic Michael reaction catalysts which tend to cause trans-esterification. The reaction is as follows:

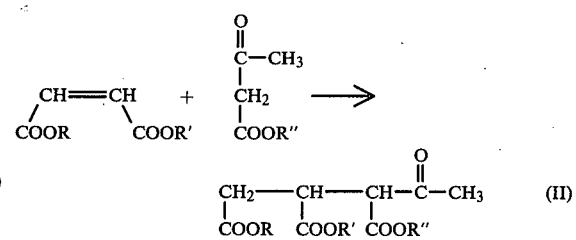

The compounds of formula (II) can be converted into compounds of formula (I) by halogenating them in a medium where (II) is soluble or partially soluble, such as water or water/methanol, respectively. Where Q is chlorine, a dilute sodium hypochlorite solution may be slowly added, while the pH is maintained at 2–8, preferably 4–5. Where Q is bromine, liquid bromine may be added slowly, with the pH maintained in the same range as for chlorine. Preferred for maintaining pH are alkali-metal hydroxides, carbonates and bicarbonates. Preferable reaction temperatures are 0°–50° C., with 25°–30° C. most preferred.

After addition of the halogenating agent, the reaction may be monitored by periodic sampling and NMR analysis, since the frequency of the methyl ketone and methylene protons shift from higher to lower field as the reaction proceeds. Isolation of the compounds of formula (I) can be accomplished by conventional techniques, such as extraction with methylene chloride.

PREPARATION OF CITRIC ACID

The compounds of formula (I) are converted to citric acid either continuously or batchwise under pressure at elevated temperatures of at least 160° C. and preferably in the range from about 160° C. to about 300° C. and most preferably at about 175° C. to about 250° C. The pressure under which the reaction takes place is not critical to the process provided the temperature conditions are met. The pressure will normally correspond approximately to the vapor pressure of the aqueous medium being employed at the temperature being utilized for the reaction. The pressure may also be enhanced by inclusion of relatively volatile inert organic solvents in the reaction medium or by prepressurizing the autoclave with an inert gas such as nitrogen prior to heating the reaction mixture to reaction temperature. Again, as stated previously, the important parameter is the temperature of the reaction and not the pressure.

Standard autoclave equipment may be used in carrying out the process of the invention. The alkaline nature of the process is advantageous in that it enables one to utilize steel and stainless steel as materials of construction for the autoclave without the need for resorting to more expensive materials of construction.

The preferred alkaline earth metal hydroxides for use in the instant process are calcium hydroxide and magnesium hydroxide. Preferably, enough hydroxide is added to bring the pH to about 11.3 to about 12.5 for calcium hydroxide and about 9 to about 10 for magnesium hydroxide. This generally represents a molar ratio of hydroxide to ester of greater than about 2.5:1 when R' is methyl, ethyl or propyl. When R' is H, Na, Li, K, $Mg_{\frac{1}{2}}$, $Ca_{\frac{1}{2}}$, $Ba_{1/8}$ or $Sr_{\frac{1}{2}}$, a ratio of over 2 moles to 1 is required. It should be recognized that the particular pH at which the reaction occurs is not critical except in order to obtain optimum reaction rates and to avoid degradation reactions the pH range referred to above is preferred. Certainly one skilled in the art would only need to do nominal experimentation to avoid those pH's at which the citrate salt would be forming at an impractically slow rate or was undergoing extensive degradation reactions after formation. It will also be apparent that the corresponding alkaline earth metal oxides may also be used in the process inasmuch as the reaction medium contains water which will immediately convert the oxides into the desired hydroxide form.

Alkali metal hydroxides such as sodium hydroxide, potassium hydroxide and lithium hydroxide may be used in partial replacement of the excess alkaline earth metal hydroxide utilized to attain an alkaline pH. Use of the alkali metal hydroxides is a less preferred mode, however, since the alkali metal hydroxides promote degradation reactions.

The compounds of formula (I) may be completely dissolved, partially dissolved or merely dispersed in the water medium at reaction temperature. The amount of water is not critical but should be sufficient to provide the water of hydration as well as excess water to allow the reaction medium to be stirred readily and thereby facilitate heat transfer from the reactor or heat exchanger into the reaction medium. A convenient range of the molar ratio of water to the formula (I) compound present in the reaction mixture is from about 5 to 1 to about 500 to 1.

Mixed reaction media containing water and an inert organic liquid or mixture of liquids may also be used as the aqueous medium for the reaction. One inert organic liquid which does not interfere with the reaction, for example, is t-butanol which may be employed in mixtures with water as the reaction medium. When a mixed reaction media is utilized the major criteria is that sufficient water must be present in the original medium or must be generated by the reactant as for example during isomerization to hydrate double bonds formed during the reaction. The amount required can be readily determined by one skilled in the art.

The reaction time for the process is in the range of a few minutes to about 8 hours depending on the temperature of the reaction and the desired degree of conversion. In general, long reaction times are less desirable since under reaction conditions, a slow decomposition of the citrate may occur, especially if alkali metal hydroxides are present in the reaction mixture. A reaction time of about $1\frac{1}{2}$–$2\frac{1}{2}$ hours at 250° C. is a typical reaction time.

While not wishing to be held to a particular theory, it is speculated that the following reactions occur:

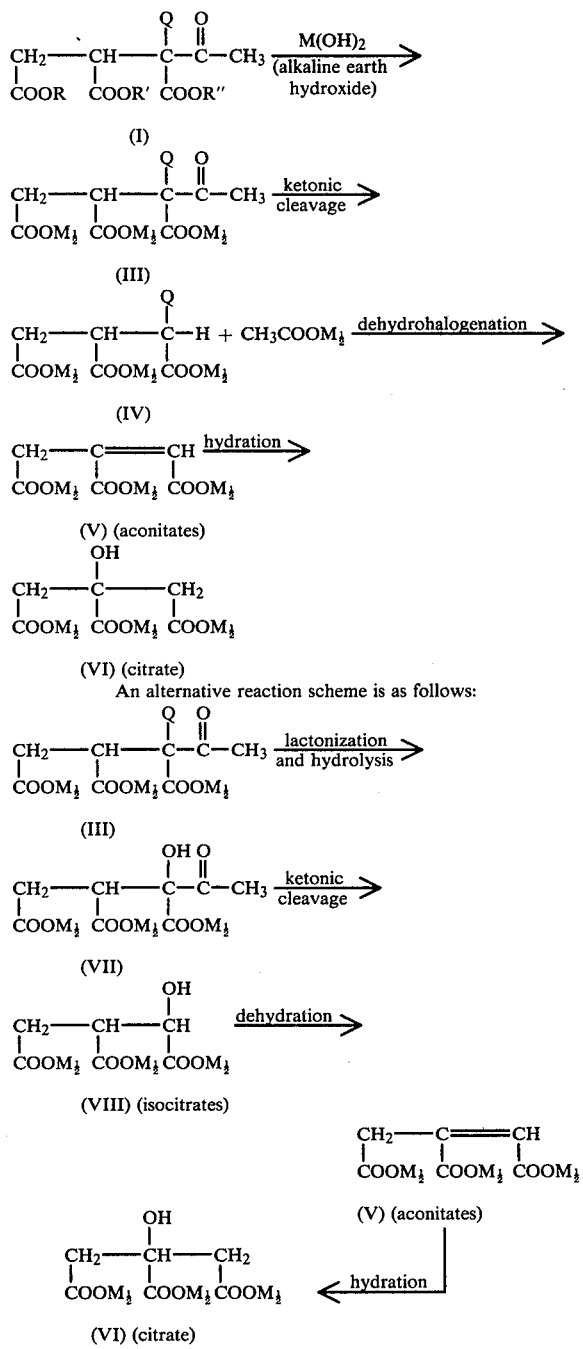

Isolation of citric acid from the reaction mixtures of the process of the invention as explained above is readily carried out by conventional methods known to the art. The most preferred reaction mixtures, for example, may contain in addition to calcium citrate and calcium halides small amounts of the calcium salts of the following carboxylic acids: succinic acid, acetic acid and oxalic acid. All of the possible products can be separated from each other by methods known to the art. A few of these methods are summarized briefly as follows:

1. The known method of purifying citric acid via its calcium salt is employed. This method is set forth in Kirk-Othmer, Encyclopedia of Chemical Technology, Vol. 4, pp. 12-17 Interscience, 1949, which is incorporated herein by reference. Thus, the reaction mixture obtained in the process of the invention, when the calcium salts are utilized, is first filtered to obtain a cake of the calcium salts of citric acid and the accompanying acids together with calcium hydroxide. The cake is then washed with hot water to remove the more soluble salts of calcium such as the halides, acetate and succinate. The cake is then treated with sulfuric acid to precipitate calcium sulfate which then, together with other insoluble calcium salts, is removed by filtration. The resulting liquid filtrate may then be treated in a variety of ways to recover pure citric acid. For example, (a) the filtrate may be subjected to ion exchange chromatography or electrodialysis using an ion exchange membrane to separate the acids directly, (b) the filtrate may be sequentially extracted; first, partially extracted with a suitable solvent such as methyl isobutyl ketone to remove undesirable carboxylic acids, followed by extraction with butanol or 2-butanol to isolate the citric acid, (c) the filtrate may be extracted with a solvent such as 2-butanol to recover a crude citric acid which is then recrystallized from a suitable solvent such as a mixture of chloroform and acetone, (d) the filtrate may be concentrated and crystallized to produce a purified citric acid which, if desired, may be recrystallized again from an aqueous medium or from a suitable organic solvent such as a mixture of chloroform and acetone to produce pure citric acid, and (e) the filtrate may be concentrated and treated with a mixture of a lower alkanol such as methanol and sulfuric acid to convert all carboxylic compounds to the ester forms which can then be isolated and separated by fractional distillation.

2. In another method, the reaction mixture (Ca, Mg or Sr salts or mixtures thereof) from the process of the invention may be treated with a cation exchange resin to remove all metal ions. For a complete discussion of cation exchange techniques, see *DOWEX:: Ion Exchange* by the Dow Chemical Company published 1958, 1959 and 1964. The eluate is then concentrated and treated in any one of the ways described above in (1a)-(1e).

3. In yet another method, the reaction product of the process of the invention may be treated with an alkali metal carbonate (e.g. sodium carbonate) to precipitate all alkaline earth metal cations as the insoluble carbonates which are then removed by filtration. The resulting filtrate containing the alkali metal salts of the carboxylic products may then be concentrated by evaporation of the water and the desired alkali metal citrate either precipitated with a water-miscible organic solvent such as for example methanol, ethanol, isopropanol and acetone as well as mixtures of such solvents or crystallized directed from the solution by cooling. Further purification of the alkali metal citrate may be accomplished by recrystallization of the salt from water alone or from mixtures of water and the aforesaid organic solvents. In general, such recrystallization will recover the alkali metal citrate in the hydrate form.

In all cases, if desired, the oxalic acid impurity may be first decomposed by the addition of an oxidizing agent to the reaction mixture or using other known means before completing the purification steps outlined above.

Having thus described the invention and its several and preferred embodiments, the following are Examples representative of the invention. All parts and proportions in the specification and claims are by weight unless otherwise indicated. Modifications, of course, will occur to those skilled in the art in view of the disclosure herein and the invention is not limited to the Examples shown.

In the Examples below the compositions of the citric acid products are determined by NMR analysis (Varian T60 instrument) using $D_2O$ as the solvent and potassium biphthalate as the internal standard. All parts and percentages herein are by weight unless otherwise specified. All pH measurements are taken at room temperature, i.e. 25° C.

EXAMPLE I

Preparation of Trimethyl Acetotricarballylate 120 grams of methyl acetoacetate (1.03 moles) and 144 grams (1 mole) of dimethyl maleate are mixed in a 500 ml flask equipped with stirrer and drying tube. Ten grams (0.19 moles) of dry sodium methoxide are added to the reaction mixture and the mixture is stirred at 45° C. for 2½ hours. The solution is cooled and 18.5 grams conc. hydrochloric acid is added dropwise until the yellow solution turns clear. 300 ml of acetone are added, the mixture is filtered of sodium chloride and the acetone solution is evaporated down under vacuum to remove acetone and unreacted acetoacetic and maleic esters. 176 grams (67% yield) of product is obtained.

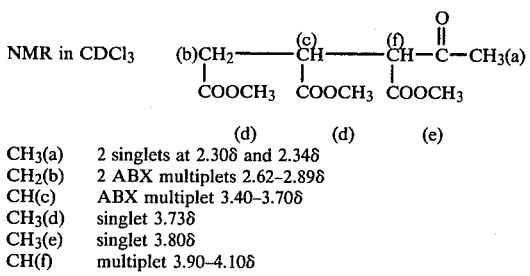

| | | |
|---|---|---|
| $CH_3(a)$ | 2 singlets at 2.30δ and 2.34δ | |
| $CH_2(b)$ | 2 ABX multiplets 2.62-2.89δ | |
| CH(c) | ABX multiplet 3.40-3.70δ | |
| $CH_3(d)$ | singlet 3.73δ | |
| $CH_3(e)$ | singlet 3.80δ | |
| CH(f) | multiplet 3.90-4.10δ | |

EXAMPLE II

Preparation of Trimethyl Acetotricarballylate 14.4 grams (0.1 mole) of dimethyl fumarate are placed into 15.5 grams (0.13 mole) of methyl acetoacetate in a 100 ml flask equipped with stirrer and drying tube. One gram (0.018 mole) $NaOCH_3$ is added and the mixture is heated to 50°-55° C. for one hour. 1.8 g conc. hydrochloric acid is added dropwise followed by 100 ml of acetone. The solution is filtered and evaporated under vacuum to remove unreacted fumarate and acetoacetate esters. 22 grams (85% yield) of product is obtained having an NMR identical to that of Example I.

EXAMPLE III

Preparation of Triethyl Acetotricarballylate

Into a 500 ml, one neck Erlenmeyer flask equipped with stirrer and drying tube is placed 103.2 grams (0.6 mole) of diethyl fumarate and 78 grams (0.6 mole) of ethyl acetoacetate. Six grams (0.088 mole) of freshly prepared sodium ethoxide is added slowly and the yellow solution is heated to 40°–45° C. for 15 minutes. The solution is then cooled to 10° C. and 9 grams conc. hydrochloric acid is dropped slowly into the solution followed by the addition of 400 ml of acetone. The acetone solution is filtered and evaporated down under vacuum. 174.8 grams (96% yield) of product is obtained.

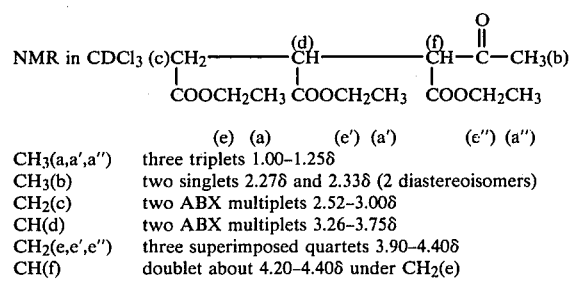

| | |
|---|---|
| $CH_3(a,a',a'')$ | three triplets 1.00–1.25$\delta$ |
| $CH_3(b)$ | two singlets 2.27$\delta$ and 2.33$\delta$ (2 diastereoisomers) |
| $CH_2(c)$ | two ABX multiplets 2.52–3.00$\delta$ |
| $CH(d)$ | two ABX multiplets 3.26–3.75$\delta$ |
| $CH_2(e,e',e'')$ | three superimposed quartets 3.90–4.40$\delta$ |
| $CH(f)$ | doublet about 4.20–4.40$\delta$ under $CH_2(e)$ |

EXAMPLE IV

Preparation of Methyl Hydrogen α-(Acetyl Carbomethoxy methinyl)-succinate 95 grams (0.63 mole) of sodium methyl maleate are placed into 200 grams (1.7 mole) of methyl acetoacetate. The mixture is heated to 110°–115° C. for two hours and then allowed to come to room temperature. 200 ml of water is added followed by 63 grams (0.63 mole) conc. hydrochloric acid diluted to 120 ml with water. The solution is evaporated under vacuum to remove all traces of methyl acetoacetate. The residue is dissolved in 200 ml of acetone, filtered and the acetone solution is evaporated to a light brown syrup. 150 grams (97% yield) of product is obtained.

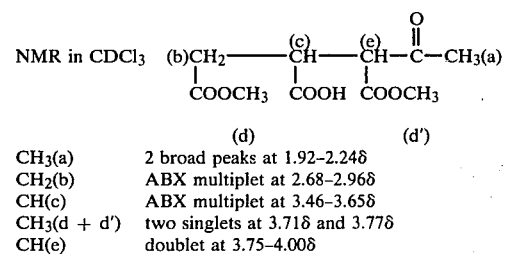

| | |
|---|---|
| $CH_3(a)$ | 2 broad peaks at 1.92–2.24$\delta$ |
| $CH_2(b)$ | ABX multiplet at 2.68–2.96$\delta$ |
| $CH(c)$ | ABX multiplet at 3.46–3.65$\delta$ |
| $CH_3(d + d')$ | two singlets at 3.71$\delta$ and 3.77$\delta$ |
| $CH(e)$ | doublet at 3.75–4.00$\delta$ |

EXAMPLE V

Preparation of Chloro Trimethyl Acetotricarballylate 243 grams (0.93 moles) of trimethyl acetotricarballylate as prepared in Example I are dissolved in 200 ml of methanol. Two kilograms of 5% sodium hypochlorite solution is added slowly while the pH is maintained at 4.5–5.0 with the gradual addition of 200 ml of 18% hydrochloric acid. After all the hypochlorite is added, the product is extracted with 400 ml of methylene chloride. 219 grams of product is recovered (84% yield).

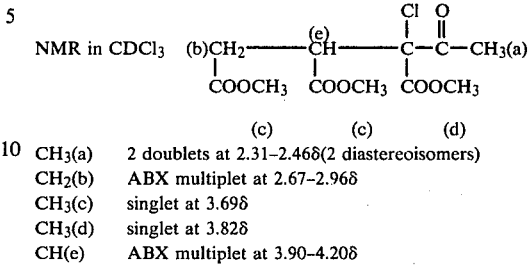

| | |
|---|---|
| $CH_3(a)$ | 2 doublets at 2.31–2.46$\delta$(2 diastereoisomers) |
| $CH_2(b)$ | ABX multiplet at 2.67–2.96$\delta$ |
| $CH_3(c)$ | singlet at 3.69$\delta$ |
| $CH_3(d)$ | singlet at 3.82$\delta$ |
| $CH(e)$ | ABX multiplet at 3.90–4.20$\delta$ |

EXAMPLE VI

Preparation of Bromo Trimethyl Acetotricarballylate 49 grams (0.19 mole) of trimethyl acetotricarballylate as prepared in Example II are dissolved in a mixture of 150 ml of methanol and 100 ml of water. 34 grams (0.21 mole) of liquid bromine is added dropwise and slowly, while the pH is maintained at 4–5 with the gradual addition of 16 grams of powdered sodium bicarbonate. After all the bromine is added, a slight orange color persists. The product is extracted out with 500 ml methylene chloride and recovered by removal of solvent under reduced pressure. 55 grams (85.4% yield).

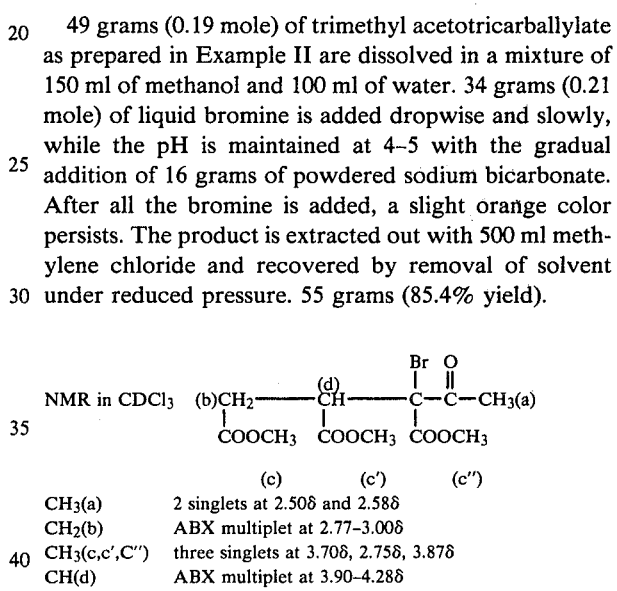

| | |
|---|---|
| $CH_3(a)$ | 2 singlets at 2.50$\delta$ and 2.58$\delta$ |
| $CH_2(b)$ | ABX multiplet at 2.77–3.00$\delta$ |
| $CH_3(c,c',C'')$ | three singlets at 3.70$\delta$, 2.75$\delta$, 3.87$\delta$ |
| $CH(d)$ | ABX multiplet at 3.90–4.28$\delta$ |

EXAMPLE VII

Preparation of Chloro Triethyl Acetotricarballylate 174.8 grams (0.58 mole) of triethyl acetotricarballylate prepared as in Example III are dissolved in 100 ml of methanol. Two kilograms of 5.0% sodium hypochlorite solution is added slowly while the pH is maintained at 4.5–5.0 with 75 grams of 15% hydrochloric acid. After the addition of the hypochlorite, the product is extracted out with 400 ml of methylene chloride and the solvent distilled under reduced pressure. 185.3 grams (95.5% yield) of product is obtained.

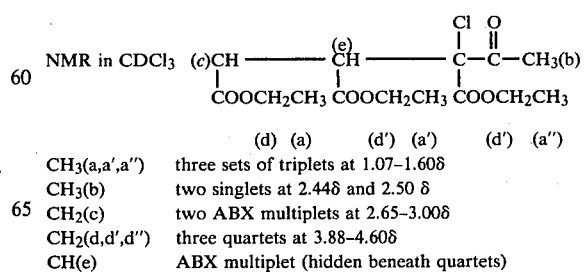

| | |
|---|---|
| $CH_3(a,a',a'')$ | three sets of triplets at 1.07–1.60$\delta$ |
| $CH_3(b)$ | two singlets at 2.44$\delta$ and 2.50 $\delta$ |
| $CH_2(c)$ | two ABX multiplets at 2.65–3.00$\delta$ |
| $CH_2(d,d',d'')$ | three quartets at 3.88–4.60$\delta$ |
| $CH(e)$ | ABX multiplet (hidden beneath quartets) |

EXAMPLE VIII

Preparation of Methyl Hydrogen α-(Acetyl Chloro Carbomethoxy Methinyl) Succinate Seventy grams (0.28 mole) of methyl hydrogen α-(acetyl carbomethoxy methinyl)-succinate as prepared in Example IV are dissolved in 200 ml of water. Eight grams (0.095 mole) of powdered sodium bicarbonate are added to a pH of 4.2. 530 grams of 5% sodium hypochlorite solution are added slowly while maintaining the pH between 4.5 to 5.0 with 25 ml of 18% hydrochloric acid. 60 ml of 18% hydrochloric acid are then added to bring the pH to 1.5. 400 ml of methylene chloride are added to extract out the product and after distillation of the solvent, 63.2 grams of product (81% yield) is obtained.

NMR in CDCl₃

$$(b)CH_2\text{---}\overset{(d)}{CH}\text{---}\overset{\overset{Cl}{|}}{C}\text{---}\overset{\overset{O}{\|}}{C}\text{---}CH_3(a)$$
$$|\qquad |\qquad |$$
$$COOCH_3\quad COOH\quad COOCH_3$$
$$(c)\qquad\qquad (c')$$

| | |
|---|---|
| $CH_3(a)$ | 2 peaks at 2.13–2.56δ |
| $CH_2(b)$ | ABX multiplet at 2.66–3.00δ |
| $CH_3(c,c')$ | 2 singlets at 3.83δ and 3.93δ |
| $CH_2(d)$ | ABX multiplet at 4.00–4.30δ |

EXAMPLE IX

Preparation of Citric Acid

Thirty grams (0.1 mole) of chloro trimethyl acetotricarballylate as prepared in Example V are placed into a one liter Parr Bomb along with 33.5 g (0.45 mole) Ca(OH)₂ and 360 ml of water. The mixture is heated to 200° C. (260 psi) for six hours (pH at this point is 11.8–11.9). The contents of the bomb are poured onto a cationic exchange column and the eluate and washings are evaporated to dryness in vacuo.

18.5 grams of product are obtained containing 95.7% citric acid (92% yield) and 3.1% succinic acid. MNR (D₂O):
 doublet at 2.8–3.0δ: —CH₂—(citric acid)
 singlet at 2.58δ: —CH₂—(succinic acid)

EXAMPLE X

Preparation of Citric Acid

Thirty grams (0.1 mole) of chloro trimethyl acetotricarballylate as prepared in Example V are placed into a one liter Parr Bomb along with 32 grams (0.43 mole) of Ca(OH)₂ and 300 ml of water. The contents of the bomb are heated to 250° C. (700 psi) for one and a half hours. The heat is turned off and the bomb is allowed to cool to room temperature. The contents of the bomb (pH 11.8) are passed through a cationic exchange column and the eluate and washings are evaporated to dryness in vacuo. 17.1 grams of product are obtained containing:
80% citric acid (71% yield)
4% succinic acid
NMR (D₂O): same as in Example IX

EXAMPLE XI

Preparation of Citric Acid

Thirty grams (0.1 mole) of chloro trimethyl acetotricarballylate as prepared in Example V are placed into a one liter Parr Bomb along with 20 grams (0.5 mole) magnesium oxide and 350 ml of water. The mixture is heated to 175° C. for six hours, cooled and then passed through a cationic exchange column. The eluate and washings are evaporated to dryness in vacuo. Sixteen grams of product are obtained containing:

48.8% citric acid (41% yield): doublet @ 2.8–3.0δ

9.5% citraconic acid
$$\left[\begin{array}{c} H(b)\qquad CH_3(a)\\ \diagdown\;\diagup\\ \|\\ \diagup\;\diagdown\\ COOH\quad COOH \end{array}\right]$$
$CH_3(a)$ singlet @2.0–2.2δ
$CH(b)$ singlet @5.84δ

4.2% citramalic
$$\left[\begin{array}{c} \overset{OH}{|}\\ \overset{(b)}{CH_2}\text{---}\overset{|}{C}\text{---}\overset{(a)}{CH_3}\\ |\quad\;\;|\\ COOH\;\;COOH \end{array}\right]$$
$CH_3(a)$ singlet @1.40δ
$CH_2(b)$ doublet of doublets @2.50–3.20δ

20.5% itaconic acid
$$\left[\begin{array}{c} \overset{(a)}{CH_2}\text{---}C=\overset{(b)}{CH_2}\\ |\qquad\;\;|\\ COOH\;\;COOH \end{array}\right]$$
$CH_2(a)$ singlet @3.38δ
$CH_2(b)$ two singlets @5.80 and 6.30δ

20.5% aconitic acid
$$\left[\begin{array}{c} \overset{(a)}{CH_2}\text{---}C=C\diagup^{COOH}_{H(b)}\\ |\qquad\;\;|\\ COOH\;\;COOH \end{array}\right]$$
$CH_2(a)$ singlet @3.82δ
$CH(b)$ singlet @7.00δ

EXAMPLE XII

Preparation of Citric Acid 33.9 (0.1 mole) grams of bromo trimethyl acetotricarballylate as prepared in Example VI are placed into a one liter Parr Bomb with 350 ml of water and 33 g (0.45 mole) Ca(OH)₂. The contents of the flask are heated to 200° C., 260 psi for six hours. The bomb is allowed to cool and the contents (pH 11.8) are passed through a cationic exchange column. The eluate and washings are evaporated to dryness. 16 grams of product is obtained containing 83.6% citric acid (70% yield) and 8.0% succinic acid. NMR (D₂O): same as in Example IX.

EXAMPLE XIII

Preparation of Citric Acid 33.6 grams (0.1 mole) of chloro trimethyl acetotricarballylate as prepared in Example VII are placed into a one liter Parr Bomb with 33 grams (0.45 mole) Ca(OH)₂. The contents of the bomb are heated to 200° C. (260 psi) for six hours. The contents, after cooling, are passed through a cationic exchange column and the eluate and washings are evaporated to dryness in vacuo. 17.1 grams product containing 94.8% citric acid (84.4% yield) and 2.5% succinic acid are obtained. NMR(D₂O): same as in Example IX.

EXAMPLE XIV

Preparation of Citric Acid

Twenty eight grams (0.1 mole) of methyl hydrogen α-(acetyl chloromethoxy methinyl) succinate as prepared in Example VIII are placed into a one liter Parr Bomb along with 34 g (0.45 mole) Ca(OH)₂ and 270 ml of water. The contents of the bomb are heated to 200° C. (260 psi) for six hours. The bomb is cooled and the contents (pH 11.8) are passed through a cationic exchange column. The eluate and washings are evaporated to dryness in vacuo. 16.5 grams of product are obtained containing 85.3% citric acid (73.3% yield) and 5.3% succinic acid. NMR(D$_2$O): same as in Example IX. Some other unidentified impurities are also present at 2.3δ and 1.4–1.8δ.

This invention has been described with respect to certain preferred embodiments and various modifications thereof will occur to persons skilled in the art and are to be included with the spirit and purview of this application and the scope of the claims.

What is claimed is:

1. A process for producing alkaline earth metal salts of citric acid comprising reacting by heating in an aqueous medium at a temperature of at least about 160° C., a compound of the formula

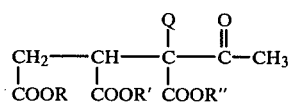

wherein

R is methyl, ethyl, or propyl;
R' is methyl, ethyl, propyl, H, Na, Li, K, Mg½ Ca½, Ba½, or Sr½;
R" is methyl, ethyl, or propyl; and
Q is chlorine or bromine;

with an alkaline earth metal hydroxide.

2. The process of claim 1 wherein said temperature is about 160° C. to about 300° C.

3. The process of claim 1 wherein said temperature is about 175° C. to about 250° C.

4. The process of claim 1 wherein the molar ratio of said alkaline earth metal hydroxide to said compound is greater than about 2 to 1.

5. The process of claim 2 wherein said compound is of the formula

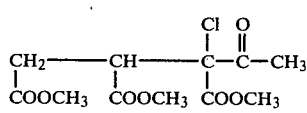

6. The process of claim 2 wherein said compound is of the formula

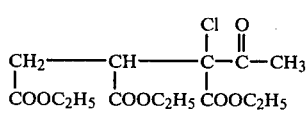

7. The process of claim 2 wherein said compound is of the formula

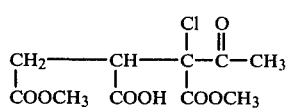

8. The process of claim 2 wherein said compound is of the formula

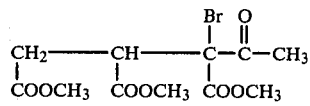

9. The process of claim 1 wherein said alkaline earth metal hydroxide is calcium hydroxide or magnesium hydroxide.

10. The process of claim 2 wherein said alkaline earth metal hydroxide is magnesium hydroxide or calcium hydroxide.

11. The process of claim 5 wherein said alkaline earth metal hydroxide is calcium hydroxide.

12. The process of claim 6 wherein said alkaline earth metal hydroxide is calcium hydroxide.

13. The process of claim 8 wherein said alkaline earth metal hydroxide is calcium hydroxide.

14. A process for producing citric acid comprising:

a. reacting, by heating in an aqueous medium at a temperature of at least about 160° C., a compound of the formula

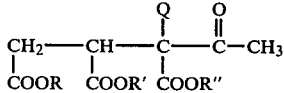

wherein

R is methyl, ethyl, or propyl;
R' is methyl, ethyl, propyl, H, Na, Li, K, Mg½, Ba½ or Sr½;
R" is methyl, ethyl, or propyl; and
Q is chlorine or bromine;

with an alkaline earth metal hydroxide; and (b) removing the alkaline earth metal ions from the reaction product of (a) and (c) isolating the citric acid from the treated reaction product of (b).

15. The process of claim 14 wherein said removal of said alkaline earth metal ions is accomplished by contacting said reaction product with a cationic exchange resin.

16. A compound of the formula

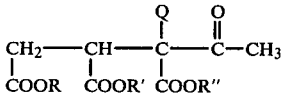

wherein

R is methyl, ethyl, or propyl;
R' is methyl, ethyl, propyl, H, Na, K, Li, Mg½, Ca½, Ba½, or Sr½;
R" is methyl, ethyl, or propyl; and
Q is chlorine or bromine.

17. A compound as in claim 16 of the formula

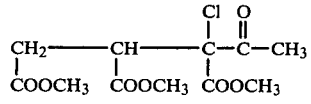

18. A compound as in claim 16 of the formula

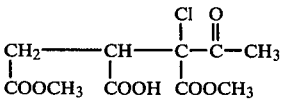

* * * * *

UNITED STATES PATENT AND TRADEMARK OFFICE
CERTIFICATE OF CORRECTION

PATENT NO. : 4,324,906
DATED : April 13, 1982
INVENTOR(S) : Eddie N. Gutierrez and Vincent Lamberti It is certified that error appears in the above—identified patent and that said Letters Patent is hereby corrected as shown below:

Column 1, line 7: change "cirtric" to --citric--.

Column 8, line 59-63: change

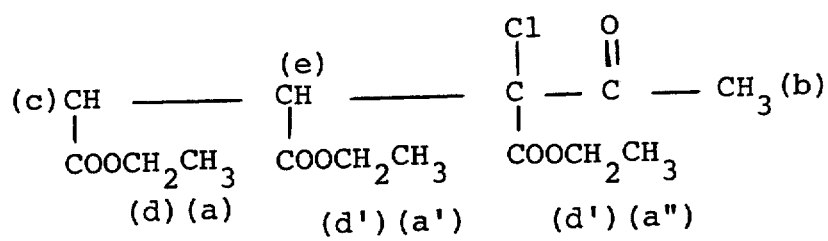

to

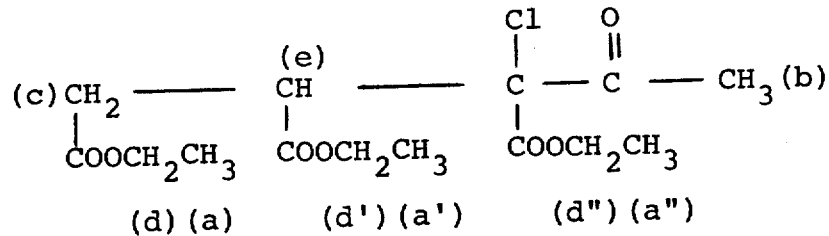

Column 9, line 41: change "MNR" to --NMR--.

UNITED STATES PATENT AND TRADEMARK OFFICE
CERTIFICATE OF CORRECTION

PATENT NO. : 4,324,906
DATED : April 13, 1982
INVENTOR(S) : Eddie N. Gutierrez etal.

It is certified that error appears in the above—identified patent and that said Letters Patent is hereby corrected as shown below:

Column 10, line 48: change "chloro trimethyl" to

-- chloro triethyl --.

Signed and Sealed this

Sixth Day of July 1982

[SEAL]

Attest:

Attesting Officer

GERALD J. MOSSINGHOFF

Commissioner of Patents and Trademarks